(12) United States Patent
Iizuka

(10) Patent No.: US 9,750,919 B2
(45) Date of Patent: Sep. 5, 2017

(54) SLEEP CONTROL DEVICE AND SLEEP CONTROL METHOD

(71) Applicant: TOYOTA JIDOSHA KABUSHIKI KAISHA, Toyota-shi (JP)

(72) Inventor: Hisashi Iizuka, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 132 days.

(21) Appl. No.: 14/432,888

(22) PCT Filed: Nov. 29, 2012

(86) PCT No.: PCT/JP2012/080954
§ 371 (c)(1),
(2) Date: Apr. 1, 2015

(87) PCT Pub. No.: WO2014/083657
PCT Pub. Date: Jun. 5, 2014

(65) Prior Publication Data
US 2015/0273177 A1   Oct. 1, 2015

(51) Int. Cl.
*A61M 21/02* (2006.01)
*A61B 5/00* (2006.01)
(Continued)

(52) U.S. Cl.
CPC ......... *A61M 21/02* (2013.01); *A61B 5/02055* (2013.01); *A61B 5/4812* (2013.01); *A61B 5/7275* (2013.01); *A61B 5/01* (2013.01); *A61B 5/021* (2013.01); *A61B 5/024* (2013.01); *A61B 5/0476* (2013.01); *A61B 5/0531* (2013.01);
(Continued)

(58) Field of Classification Search
CPC .......... A61M 2230/16; A61M 2230/42; A61M 2230/50; A61M 2230/30; A61M 2205/3303; A61M 2021/0083; A61M 2230/005; A61M 2230/06; A61B 5/02055; A61B 5/7275; A61B 5/7246; A61B 5/4812; A61B 5/11; A61B 5/08; A61B 5/0531; A61B 5/0476; A61B 5/024; A61B 5/021
See application file for complete search history.

(56) References Cited

U.S. PATENT DOCUMENTS

2012/0133513 A1   5/2012   Wada et al.
2013/0181841 A1   7/2013   Iizuka

FOREIGN PATENT DOCUMENTS

JP   11-78591 A       3/1999
JP   1178591 A   *   3/1999
(Continued)

OTHER PUBLICATIONS

International Search Report issued Mar. 12, 2013 in PCT/JP2012/080954.

*Primary Examiner* — Christine H Matthews
*Assistant Examiner* — Joshua D Lannu
(74) *Attorney, Agent, or Firm* — Oblon, McClelland, Maier & Neustadt, L.L.P.

(57) ABSTRACT

A sleep variable calculation portion predicts a change in a sleep depth of a sleeping subject. When the sleep variable calculation portion predicts that the subject may be in a transition state in which the sleep depth of the subject further increases at a wake-up time of the subject, a stimulus presentation device provides a stimulus to the subject at a point in time preceding the wake-up time.

9 Claims, 16 Drawing Sheets

(51) Int. Cl.
*A61B 5/0205* (2006.01)
*A61B 5/01* (2006.01)
*A61B 5/021* (2006.01)
*A61B 5/024* (2006.01)
*A61B 5/0476* (2006.01)
*A61B 5/053* (2006.01)
*A61B 5/08* (2006.01)
*A61B 5/11* (2006.01)
*A61M 21/00* (2006.01)

(52) U.S. Cl.
CPC . *A61B 5/08* (2013.01); *A61B 5/11* (2013.01); *A61B 5/7246* (2013.01); *A61M 2021/0083* (2013.01); *A61M 2205/3303* (2013.01); *A61M 2230/06* (2013.01); *A61M 2230/10* (2013.01); *A61M 2230/16* (2013.01); *A61M 2230/30* (2013.01); *A61M 2230/42* (2013.01); *A61M 2230/50* (2013.01)

(56) References Cited

FOREIGN PATENT DOCUMENTS

| | | | |
|---|---|---|---|
| JP | 2001-187146 A | | 7/2001 |
| JP | 2001187146 A | * | 7/2001 |
| JP | 2006-43304 A | * | 2/2006 |
| JP | 2006-43304 A | | 2/2006 |
| JP | 2009-229370 A | | 10/2009 |
| JP | 2012-65996 A | | 4/2012 |
| JP | 2012-110536 A | | 6/2012 |

* cited by examiner

SLEEP CONTROL DEVICE AND SLEEP CONTROL METHOD

TECHNICAL FIELD

An embodiment of the present invention relates to a sleep control device and a sleep control method that are for making a subject have sound sleep.

BACKGROUND ART

Techniques for making a subject have sound sleep have been suggested. For example, Patent Literature 1 discloses a device that determines whether a subject is in a state of rapid eye movement (REM) sleep or in a state of non-REM sleep by detecting brain waves of the subject. When the subject is in the state of REM sleep, the device of Patent Literature 1 wakes the subject up by providing a stimulus to the subject.

CITATION LIST

Patent Literature

[Patent Literature 1] Japanese Unexamined Patent Application Publication No. 2012-110536

SUMMARY OF INVENTION

Technical Problem

However, even with the aforementioned technique, the awakened subject has a low level of consciousness in some cases. Therefore, the technique needs to be further improved.

An embodiment of the present invention is focused on the above problem, and an object thereof is to provide a sleep control device and a sleep control method that make a subject highly likely to be able to have sounder sleep.

Solution to Problem

An embodiment of the present invention is a sleep control device including a sleep depth prediction unit configured to predict a change in a sleep depth of a sleeping subject; and a stimulus providing unit configured to provide a stimulus to the subject at a second time preceding a first time, when the sleep depth prediction unit predicts that the subject may be in a transition state in which the sleep depth of the subject further increases at the first time that is set to wake the subject up.

At the time that is set to wake the subject up, if the subject in the transition state in which the sleep depth of the subject further increases is provided with a stimulus and awakened by constraint, due to the sleep inertia that makes the level of consciousness of the awakened subject stay low, the subject cannot wake up feeling refreshed. However, according to the present constitution, the sleep depth prediction unit predicts the change in the sleep depth of the sleeping subject, and when the sleep depth prediction unit predicts that the subject may be in the transition state, in which the sleep depth of the subject further increases, at the first time that is set to wake the subject up, the stimulus providing unit provides a stimulus to the subject at the second time preceding the first time. Consequentially, the phase of the cycle of the change in the sleep depth of the subject is shifted. As a result, at the first time to wake the subject up, the subject is highly likely to be in a transition state in which the sleep depth further decreases instead of the transition state in which the sleep depth further increases, and the subject is highly likely to be able to wake up feeling more refreshed.

In this case, the stimulus providing unit can provide a stimulus to the subject at the second time that is predicted as the transition state, in which the sleep depth of the subject further decreases, by the sleep depth prediction unit.

According to the present constitution, the stimulus providing unit provides a stimulus to the subject at the second time predicted as the transition state, in which the sleep depth of the subject further decreases, by the sleep depth prediction unit. Consequentially, the phase of the cycle of the change in the sleep depth of the subject is shifted. As a result, even at the first time to wake the subject up, the subject is highly likely to be in a transition state in which the sleep depth of the subject further decreases instead of the transition state in which the sleep depth further increases, and the subject is highly likely to be able to wake up feeling more refreshed.

Furthermore, the stimulus providing unit can provide a stimulus, which does not wake the subject up until the first time, at the second time.

According to the present constitution, the stimulus providing unit provides the stimulus, which does not wake the subject up until the first time, at the second time. Consequentially, the subject is inhibited from being awakened before the first time to wake the subject up. Moreover, the subject is highly likely to be in the transition state in which the sleep depth of the subject further decreases at the first time, and the subject is highly likely to be able to wake up feeling more refreshed.

Furthermore, the sleep depth prediction unit can predict the cycle of the change in the sleep depth of the sleeping subject. In addition, in the cycle of the change in the sleep depth that is predicted by the sleep depth prediction unit, the stimulus providing unit can provide a stimulus to the subject at the second time included in a sleep depth decreasing period that is predicted as the transition state in which the sleep depth of the subject further decreases.

According to the present constitution, the sleep depth prediction unit predicts the cycle of the change in the sleep depth of the sleeping subject. Moreover, in the cycle of the change in the sleep depth that is predicted by the sleep depth prediction unit, the stimulus providing unit provides a stimulus to the subject at the second time included in a sleep depth decreasing period that is predicted as the transition state in which the sleep depth of the subject further decreases. Consequentially, the cycle of the sleep depth of the subject is more easily controlled, and the subject is highly likely to be able to wake up feeling more refreshed.

In addition, the sleep depth prediction unit predicts the cycle of the change in the sleep depth of the sleeping subject. When the sleep depth prediction unit predicts that the subject may be in the transition state, in which the sleep depth of the subject further increases, at the first time, the stimulus providing unit can provide a stimulus to the subject at the second time, such that a sleep depth increasing period closest to the first time, among sleep depth increasing periods as the transition state, in which the sleep depth of the subject further increases, in the cycle of the change in the sleep depth predicted by the sleep depth prediction unit, is further shortened.

According to the present constitution, the sleep depth prediction unit predicts the cycle of the change in the sleep depth of the sleeping subject. When the sleep depth prediction units predicts that the subject may be in the transition state, in which the sleep depth of the subject further increases, at the first time, the stimulus providing unit provides a stimulus to the subject at the second time, such that the sleep depth increasing period closest to the first time, among the sleep depth increasing periods as the transition state, in which the sleep depth of the subject further increases, in the cycle of the change in the sleep depth predicted by the sleep depth prediction unit, is further shortened. Consequentially, the sleep depth increasing period immediately before the first time to wake the subject up is shortened, and the sleep inertia, which makes the level of consciousness of the awakened subject stay low, is reduced. As a result, the subject is highly likely to be able to wake up feeling more refreshed.

Furthermore, by providing a stimulus to the subject after the second time, the stimulus providing unit can maintain the sleep depth of the subject at a sleep depth corresponding to sleep stage 1 during a period from the second time to the first time.

Moreover, by providing a stimulus to the subject after the second time, the stimulus providing unit can maintain the sleep depth of the subject at a sleep depth at which θ waves appear in brain waves of the subject during a period from the second time to the first time.

In addition, the stimulus providing unit can provide a stimulus that does not wake the subject up until the first time, after the second time that precedes the first time either by a time corresponding to 5% of sleeping hours of the subject or by 10 minutes to 20 minutes.

The sleep depth prediction unit can predict the cycle of the change in the sleep depth of the sleeping subject. Furthermore, the stimulus providing unit can provide a stimulus that does not wake the subject up until the first time, after the second time that precedes the first time by a time equal to or shorter than the time taken for the sleep depth of the subject to be maximized and then minimized in the cycle of the change in the sleep depth predicted by the sleep depth prediction unit.

According to the present constitution, for example, by providing a stimulus to the subject after the second time, the stimulus providing unit maintains the sleep depth of the subject at a sleep depth corresponding to a sleep stage 1 during a period from the second time to the first time. In sleep stage 1, θ waves appear as background brain waves. If the θ waves are caused to appear before the subject wakes up, the sleep inertia, that makes the level of consciousness of the awakened subject stay low, is reduced. Consequentially, the subject is highly likely to be able to wake up feeling more refreshed.

In the specification, claims, and drawings of the present application, "sleep stages 1 to 4" or "sleep stages I to IV" mean indices that are generally used for indicating the sleep depth, and show four kinds of the sleep depth in non-REM sleep in sleep states divided into REM sleep and non-REM sleep.

Specifically, the sleep stage 1 (sleep stage I) is a stage of transition to sleep from awake state, and in this stage, the subject can recognize the surroundings to some degree. In the sleep stage 1, as the sleep depth of the subject increases, the cerebral activity decreases, and thus the θ waves appear.

In the sleep stage 2 (sleep stage II), the sleep depth becomes greater than that of the sleep stage 1. In the sleep stage 2, among waveforms with low amplitude, characteristic waveforms called transient sleep spindles or K-complexes appear in the brain waves.

In the sleep stage 3 (sleep stage III) and the sleep stage 4 (sleep stage IV), the sleep depth becomes greater than that of the sleep stage 2. The sleep of the stages 3 and 4 is called "slow-wave sleep", and in these states, the body is repaired. Generally, about 20 minutes after falling asleep, a subject reaches the sleep stage 3 which is the onset of deep sleep, and at this stage, a decrease in body temperature or a decrease in respiration rate or heart rate is observed. In the sleep stage 3, slow waves called δ waves account for 50% of brain waves.

The sleep stage 4 is a stage of deepest sleep. Generally, in an initial sleep cycle, it takes about 1 hour for the subject to reach the sleep stage 4 after falling asleep. In the sleep stage 4, the δ waves, which have high amplitude and low frequency, account for 50% or more of brain waves.

While the subject is sleeping, generally, the sleep depth increases as sleep progresses into the sleep stage 1 in which transition to non-REM sleep from REM sleep occurs, the sleep stage 2, the sleep stage 3, and then the sleep stage 4, and decreases as sleep progresses into the sleep stage 4 as non-REM sleep, the sleep stage 3, the sleep stage 2, the sleep stage 1, and then REM sleep. This cycle lasting for about 90 minutes repeats.

Furthermore, the sleep depth prediction unit predicts a REM sleep period during which the sleeping subject has REM sleep. Based on the REM sleep period predicted by the sleep depth prediction unit, the stimulus providing unit can provide a stimulus to the subject at the second time so as to inhibit the subject from progressing into the REM sleep from the non-REM sleep.

According to the present constitution, the sleep depth prediction unit predicts the REM sleep period during which the sleeping subject has REM sleep, and based on the REM sleep period predicted by the sleep depth prediction unit, the stimulus providing unit provides a stimulus to the subject at the second time so as to inhibit the subject from progressing into the REM sleep from the non-REM sleep. During the REM sleep, muscles of the subject are relaxed, and the level of consciousness of the subject awakened from the REM sleep tends to be low. Accordingly, if the subject is inhibited from progressing into the REM sleep from the non-REM sleep, the level of consciousness of the awakened subject can be increased.

In this case, the stimulus providing unit can provide a stimulus to the subject at the second time so as to inhibit the subject from progressing into the REM sleep from the non-REM sleep during the REM sleep period closest to the first time among the REM sleep periods predicted by the sleep depth prediction unit.

According to the present constitution, the stimulus providing unit provides a stimulus to the subject at the second time so as to inhibit the subject from progressing into the REM sleep from the non-REM sleep during the REM sleep period closest to the first time among the REM sleep periods predicted by the sleep depth prediction unit. If the REM sleep of the sleeping subject is excessively suppressed, the level of consciousness of the subject who is awakening from the sleep is likely to rapidly decrease. Therefore, if the subject is inhibited from progressing into the REM sleep during the REM sleep period closest to the first time to wake the subject up among the REM sleep periods of the sleeping subject, it is possible to increase the level of consciousness of the awakened subject, and to prevent the rapid decrease in the level of consciousness of the subject who is awakening from the sleep.

In addition, the sleep depth prediction unit predicts a phasic REM sleep period during which the sleeping subject has phasic REM sleep. Based on the phasic REM sleep period predicted by the sleep depth prediction unit, the stimulus providing unit can provide a stimulus to the subject at the second time so as to inhibit the subject from progressing into the phasic REM sleep from tonic REM sleep.

According to the present constitution, the sleep depth prediction unit predicts the phasic REM sleep period during which the sleeping subject has a phasic REM sleep. Moreover, based on the phasic REM sleep period predicted by the sleep depth prediction unit, the stimulus providing unit provides a stimulus to the subject at the second time so as to inhibit the subject from progressing into the phasic REM sleep from the tonic REM sleep. The REM sleep includes a phasic period, during which the eye of the subject moves and external stimuli are blocked, and a tonic period during which the subject has feeling from outside and which is close to the sleep stage 1. As described above, if the REM sleep of the sleeping subject is excessively suppressed, the level of consciousness of the subject who is awakening from the sleep is likely to rapidly decrease. Therefore, if the subject is inhibited from progressing into the phasic REM sleep from the tonic REM sleep such that the rapid decrease in the level of consciousness of the subject, who is awakening from the sleep, resulting from the excessive suppression of the REM sleep is reduced, and such that a state closer to a natural sleep is created, it is possible to increase the level of consciousness of the awakened subject and to prevent the rapid decrease in the level of consciousness of the subject who is awakening from the sleep.

In this case, the stimulus providing unit can provide a stimulus to the subject at the second time so as to inhibit the subject from progressing into the phasic REM sleep from the tonic REM sleep during the phasic REM sleep period closest to the first time among phasic REM sleep periods predicted by the sleep depth prediction unit.

According to the present constitution, the stimulus providing unit provides a stimulus to the subject at the second time so as to inhibit the subject from progressing into the phasic REM sleep from the tonic REM sleep during the phasic REM sleep period closest to the first time among phasic REM sleep periods predicted by the sleep depth prediction unit. Consequentially, a state closer to a natural sleep can be created, and it is possible to increase the level of consciousness of the awakened subject and to prevent the rapid decrease in the level of consciousness of the subject who is awakening from the sleep.

Furthermore, the sleep depth prediction unit can predict a tonic REM sleep period during which the sleeping subject has a tonic REM sleep, and the stimulus providing unit can provide a stimulus to the subject at the second time included in the tonic REM sleep period predicted by the sleep depth prediction unit.

According to the present constitution, the sleep depth prediction unit predicts the tonic REM sleep period during which the sleeping subject has a tonic REM sleep, and the stimulus providing unit provides a stimulus to the subject at the second time included in the tonic REM sleep period predicted by the sleep depth prediction unit. Consequentially, it is possible to inhibit the subject from progressing into the phasic REM sleep while allowing the subject to have the tonic REM sleep. Furthermore, it is possible to increase the level of consciousness of the awakened subject and to prevent the rapid decrease in the level of consciousness of the subject who is awakening from the sleep.

In addition, the stimulus providing unit can provide a weaker stimulus to the subject as the time elapsing from the onset of the sleep of the subject is lengthened.

According to the present constitution, the stimulus providing unit provides a weaker stimulus to the subject as the time elapsing from the onset of the sleep of the subject is lengthened. As the sleeping hours increase, the level of an adrenocortical hormone (cortisol) is heightened. The cortisol is a hormone of which the level is heightened at a stage in which the subject is ready to be awakened from the sleep. The higher the cortisol level, the easier the subject wakes up. Therefore, if the strength of the stimulus is weakened as the sleeping hours increase and as the cortisol level increases, by providing an appropriate stimulus to the subject, it is possible to prevent the subject from waking up before the first time and to control the sleep.

Furthermore, the stimulus providing unit can provide a stimulus to the subject at the second time, based on a correlation between the time elapsing from the onset of the sleep of the subject at the second time and the strength of the stimulus.

According to the present constitution, the stimulus providing unit provides a stimulus to the subject at the second time, based on a correlation between the time elapsing from the onset of the sleep of the subject at the second time and the strength of the stimulus. Consequentially, by providing an appropriate stimulus to the subject, it is possible to prevent the subject from waking up before the first time and to control the sleep.

Moreover, an embodiment of the present invention is a sleep control method including a sleep depth prediction step of predicting a change in a sleep depth of a sleeping subject, and a stimulus providing step of providing a stimulus to the subject at a second time preceding a first time, when the subject is predicted to be in a transition state, in which the sleep depth of the subject further increases at the first time that is set to wake the subject up, in the sleep depth prediction step.

Advantageous Effects of Invention

According to the sleep control device and the sleep control method of an embodiment of the present invention, the subject is highly likely to be able to wake up feeling more refreshed.

DESCRIPTION OF EMBODIMENTS

Figure 1:
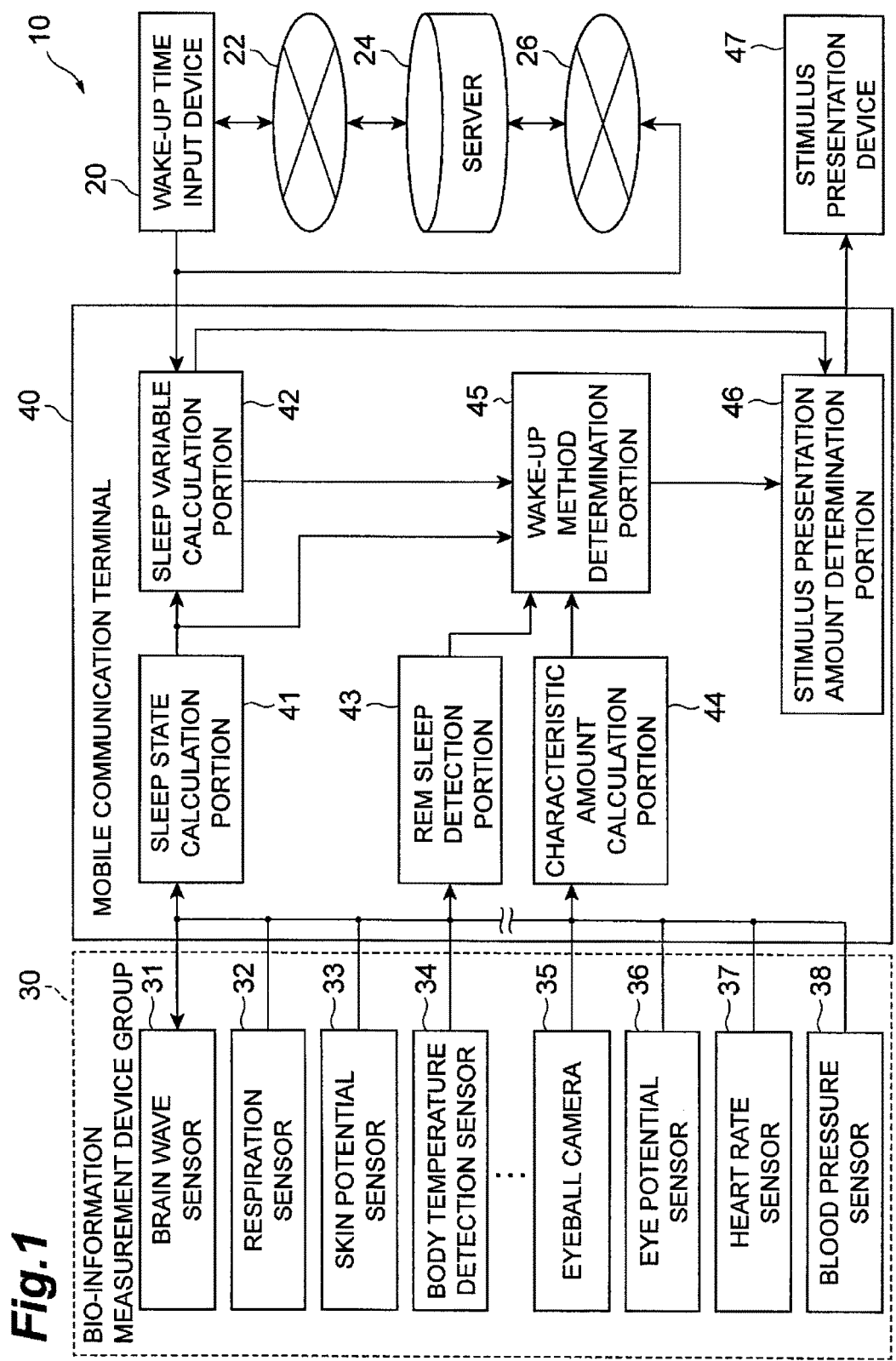
FIG. 1 is a block diagram showing a wake-up assisting system of an embodiment.

An example of the sleep control device and the sleep control method according to embodiments of the present invention will be described with reference to drawings. As shown in FIG. 1, the sleep control device of the present embodiment is constituted as a wake-up assisting system 10 and includes a wake-up time input device 20, a bio-information measurement device group 30, and a mobile communication terminal 40. The wake-up assisting system 10 of the present embodiment is used for assisting a sleeping subject to be able to wake up feeling more refreshed.

The wake-up time input device 20 obtains a length of sleeping hours or a wake-up time that a subject, who is to take a nap for a short period of time or have a sleep for a long period of time, wants. Specifically, the wake-up time input device 20 is an input terminal such as a keyboard, and sleeping hours or the wake-up time that the subject wants is directly input into the device. Furthermore, the wake-up time input device 20 can obtain the sleeping hours or the wake-up time that the subject wants, from an external storage medium such as a scheduler of server 24 which is connected to networks 22 and 26. When the sleeping hours or the wake-up time that the subject wants is not input into the wake-up time input device 20, and when the external storage medium such as the scheduler of the server 24 does not have a record of the sleeping hours or the wake-up time that the subject wants, the wake-up time input device 20 sets the wake-up time of the subject to be the usual wake-up time.

The bio-information measurement device group 30 obtains physiological information on the subject who is to take a nap for a short period of time or to sleep for a long period of time. The bio-information measurement device group 30 includes a brain wave sensor 31, a respiration sensor 32, a skin potential sensor 33, a body temperature detection sensor 34, an eyeball camera 35, an eye potential sensor 36, a heart rate sensor 37, and a blood pressure sensor 38. By using these devices, the bio-information measurement device group 30 measures one or more indices among brain waves, automatic nervous activities such as respiration, skin potential, body temperature, heart rate, and blood pressure, eye movements, and body motions of the subject that are required for determining a method for waking the subject up.

The bio-information measurement device group 30 does not necessarily use a measurement method in which each of the sensors individually measures each of the indices. For instance, the bio-information measurement device group 30 can use a contact-type measurement method in which the respiration, heart rate, body motions, and the like of the subject are measured from acceleration of the mobile communication terminal 40 such as a mobile phone. Moreover, for example, the bio-information measurement device group 30 can use a contact-type measurement method in which the respiration, heart rate, and body motion of the subject are measured by a sheet sensor such as a piezoelectric element. In addition, for example, the bio-information measurement device group 30 can use a contact-type measurement method in which the heart rate, skin potential, blood pressure, and body temperature of the subject are measured by using a watch-type sensor. Furthermore, for example, the bio-information measurement device group 30 can use a contact-type measurement method in which the brain waves, heart rate, skin potential, blood pressure, and body temperature of the subject are measured by using a band-type sensor mounted on cephalic region of the subject. Alternatively, the bio-information measurement device group 30 may use a non-contact type measurement method in which the physiological indices of the subject are measured by an ultrasonic sensor or the like.

The bio-information measurement device group 30 can also be constituted with independent sensors. For example, the brain wave sensor 31 can be constituted with a simple electro-encephalograph. Moreover, the heart rate sensor 37 and the blood pressure sensor 38 may be connected to another terminal such as a personal computer by short-range wireless communication such that the data of the measured indices are processed.

When the wake-up time that the subject wants is determined by the wake-up time input device 20, and the subject is confirmed to have fallen asleep by the physiological indices measured by the bio-information measurement device group 30, the bio-information measurement device group 30 starts to measure a sleep depth of the subject. Regarding the onset of sleep of the subject, when the physiological indices measured by the bio-information measurement device group 30 decrease for a certain period of time, for example, when the acceleration of the subject decreases for 3 minutes, it is determined that the subject has fallen asleep. Alternatively, when an absolute value of the acceleration of the subject becomes equal to or less than ½ of the acceleration input into the wake-up time input device 20 by the subject, it is determined that the subject has fallen asleep. Otherwise, respiration signals of the subject are used to determine whether the subject has fallen asleep.

Specifically, the mobile communication terminal 40 is, for example, a mobile phone or a personal computer that the subject carries. The mobile communication terminal 40 includes a sleep state calculation portion 41, a sleep variable calculation portion 42, a REM sleep detection portion 43, a characteristic amount calculation portion 44, a wake-up method determination portion 45, and a stimulus presentation amount determination portion 46 on the inside thereof, and includes a stimulus presentation device 47 on the outside thereof.

The sleep state calculation portion 41 is connected to the respective devices of the bio-information measurement device group 30 through wire or wirelessly, and processes the data measured by the respective devices.

From the respective physiological indices of the subject that are processed by the sleep state calculation portion 41, the sleep variable calculation portion 42 measures the sleep depth, the change in the sleep depth, the sleep depth predicted at any point in time, the time elapsed from the onset of a nap, the time during which a predetermined sleep depth is accumulated, and the time during which a predetermined sleep depth is maintained. The sleep variable calculation portion 42 can determine the sleep depth of the subject based on the international determination standard by using the brain waves of the subject obtained by the brain wave sensor 31. The sleep variable calculation portion 42 may estimate the sleep depth of the subject, from the respiration, skin potential, body temperature, eye movements, heart rate, blood pressure, and the like of the subject that are obtained by the respiration sensor 32, the skin potential sensor 33, the body temperature detection sensor 34, the eyeball camera 35, the eye potential sensor 36, the heart rate sensor 37, and the blood pressure sensor 38. Furthermore, the sleep variable calculation portion 42 may determine the sleep depth of the subject, from a power spectrum of brain waves and the like of the subject in any frequency band.

When used for sensing the change in the sleep depth of the subject, the sleep variable calculation portion 42 can sense the change in the sleep depth from the electrical activity of the subject's skin, from when the subject is awake to when the subject is in shallow sleep. The sleep variable calculation portion 42 can calculate the change in the sleep depth of the subject who is in shallow sleep, by combining slow eye movements of the subject, a change in the respiration pattern, such as transition to costal respiration from abdominal respiration, and the like together.

As described later, from the physiological indices such as eye movements of the subject, the REM sleep detection portion 43 detects whether the subject is in the state of REM sleep or in the state of non-REM. The REM sleep detection portion 43 predicts whether the subject is in the state of REM sleep or in the state of non-REM sleep at any point in time.

As described later, the characteristic amount calculation portion 44 calculates a characteristic amount from the physiological indices such as eye movements of the subject, and detects the sleep state so as to ascertain whether the subject is in the state of phasic REM sleep or in the state of tonic sleep.

As described later, based on the information obtained by the sleep state calculation portion 41, the sleep variable calculation portion 42, the REM sleep detection portion 43, and the characteristic amount calculation portion 44, the wake-up method determination portion 45 determines how to present a stimulus for controlling to wake the subject up and the sleep depth.

As described later, based on a map or the like, in which the correlation among a predetermined time elapsed from the onset of sleep of the subject, the strength of the stimulus, and the interval of the stimulus presentation is recorded, the stimulus presentation amount determination portion determines the amount of the stimulus to be presented to the subject.

The stimulus presentation device 47 presents a stimulus, which is for waking the subject up or for causing the subject to progress into any sleep depth, to the subject. The stimulus presentation device 47 provides a physical stimulus that the subject can perceive. For example, stimulus presentation device 47 presents a stimulus such as light, sound, vibration, heat, cold air, or smell to the subject.

Figure 2:
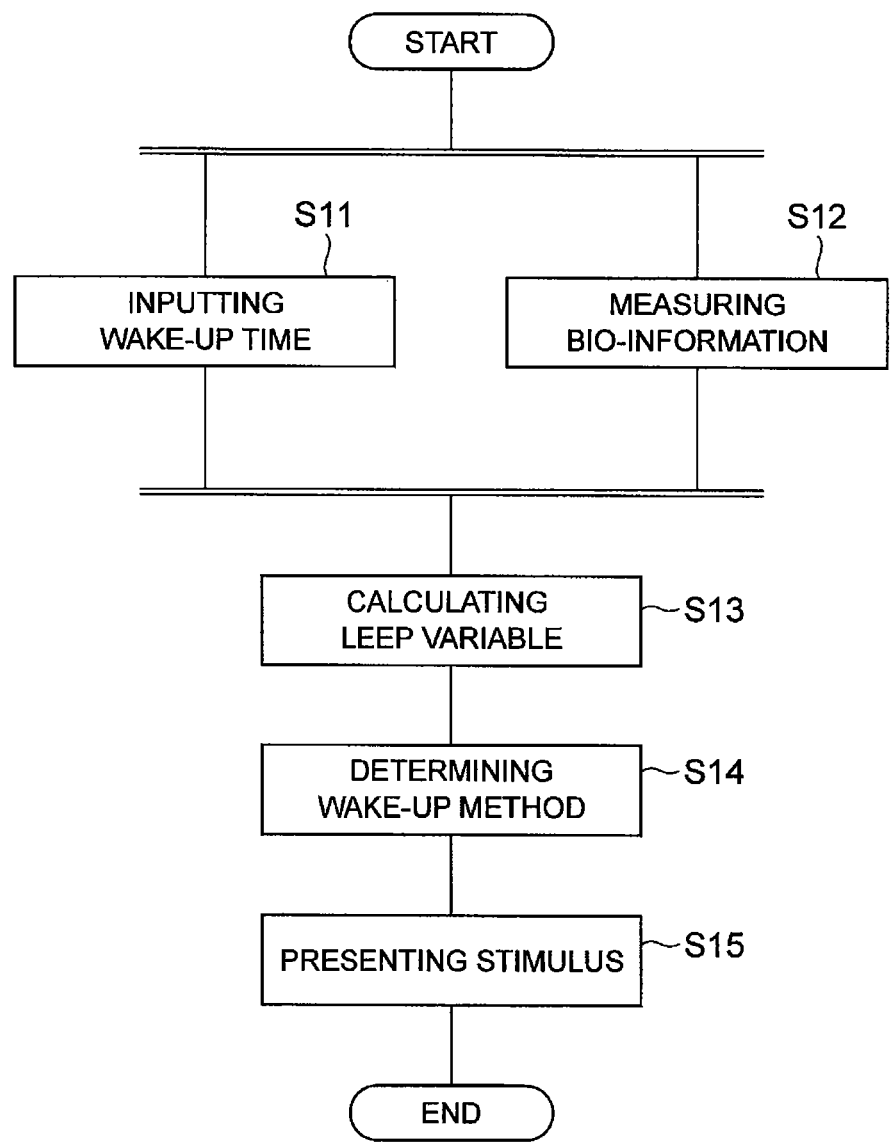
FIG. 2 is a flowchart showing the overall operation of the wake-up assisting system of the embodiment.

Hereinafter, the operation of the wake-up assisting system 10 of the present embodiment will be described. First, the overall operation of the wake-up assisting system 10 of the present embodiment will be described. As shown in FIG. 2, a subject inputs a wake-up time or sleeping hours that the subject want into the wake-up time input device 20 connected to the mobile communication terminal 40 (S11). By the bio-information measurement device group 30, physiological indices of the subject, such as brain waves, respiration, and heart rate, are measured (S12). By the sleep variable calculation portion 42, an expected sleep variable such as a sleep depth of the subject in any point in time is calculated (S13). Based on the sleep variable calculated by the sleep variable calculation portion 42, the wake-up method determination portion 45 determines a wake-up method for the subject, such as a method for making the subject start to be awakened from the sleep or a method for inducing the subject to progress into a predetermined sleep depth (S14). In order to perform the wake-up method determined by the wake-up method determination portion 45, the stimulus presentation device 47 presents a stimulus to the subject (S15).

Figure 3:
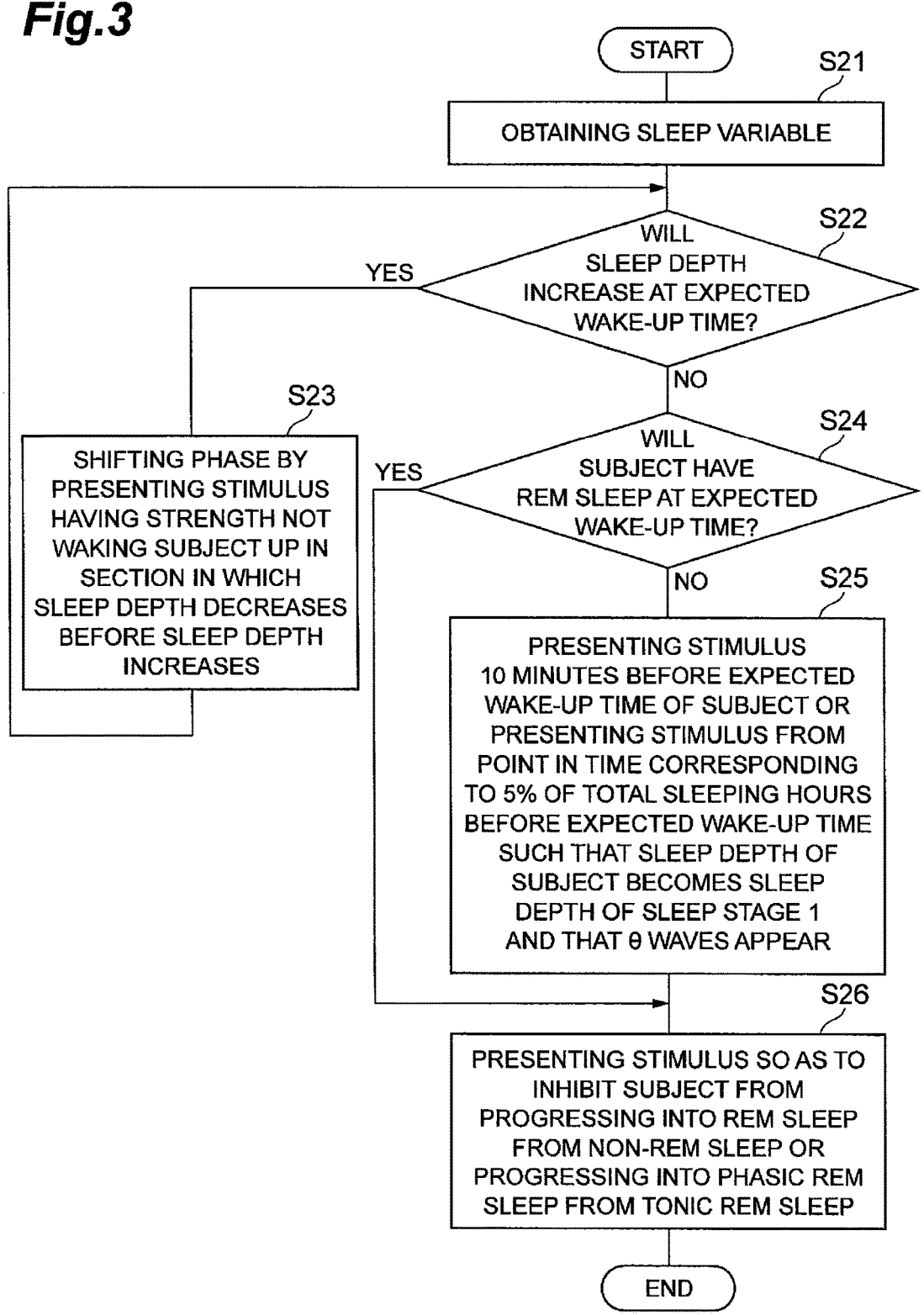
FIG. 3 is a flowchart showing the details of the operation of the wake-up assisting system of the embodiment.

Next, the details of the operation of the wake-up assisting system 10 of the present embodiment will be described. As shown in FIG. 3, by the sleep variable calculation portion 42, the sleep variable of the subject is obtained (S21). The sleep variable calculation portion 42 determines whether or not the subject is in a transition state in which the sleep depth of the subject further increases at the wake-up time that the subject wants (S22).

Figure 4:
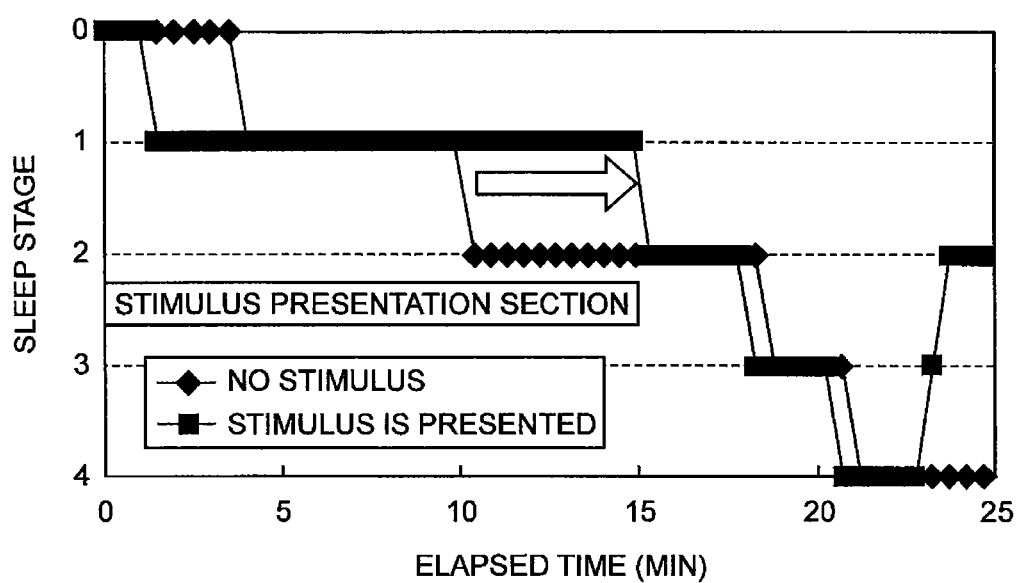
FIG. 4 is a graph showing a change in a sleep depth in a case in which a stimulus is presented and in a case in which a stimulus is not presented.
Figure 5:
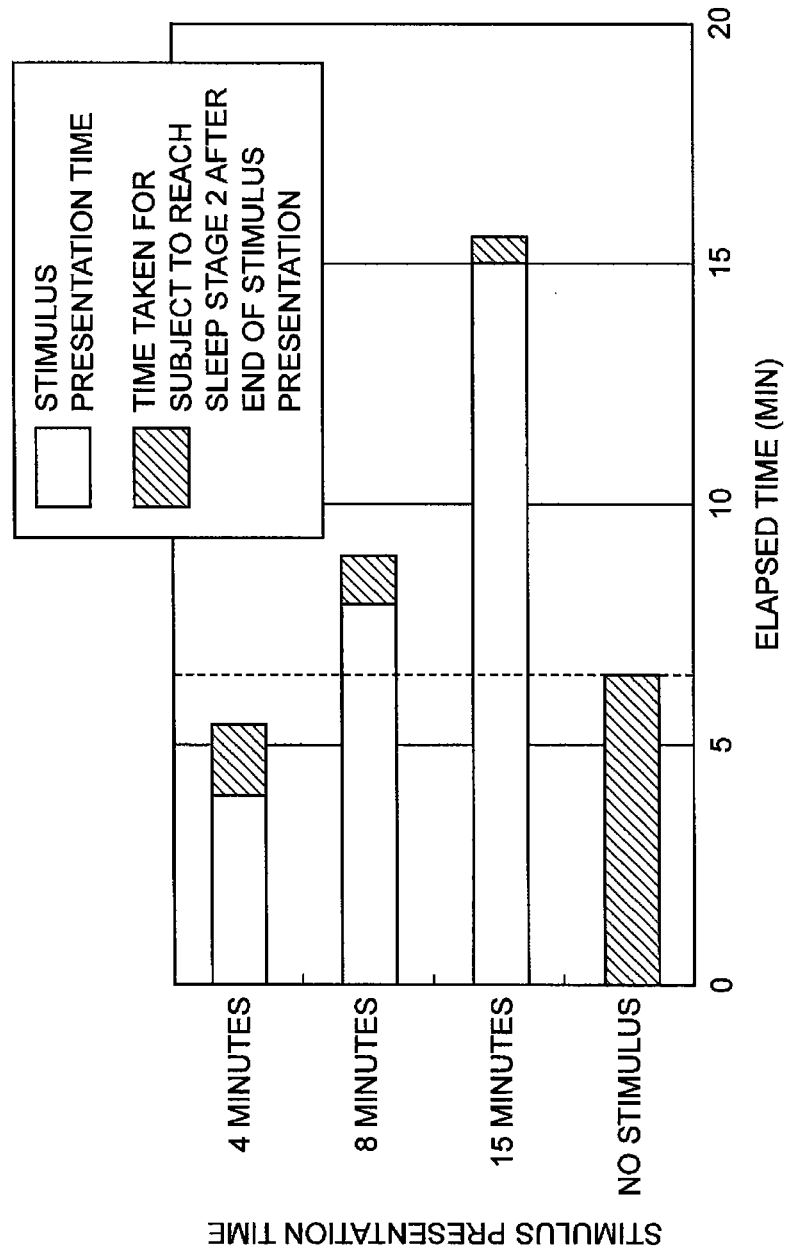
FIG. 5 is a graph showing a stimulus presentation time and a time taken for a subject to reach a sleep stage 2 after the end of the stimulus presentation.

As shown in FIG. 4, the sleep depth of the sleeping subject cyclically increases and decreases repeatedly. Such a cycle of the increase and decrease in the sleep depth is called an ultradian rhythm. In the transition state in which the sleep depth of the subject further increases, if a stimulus is provided to the subject, and thus the subject is awakened by constraint, due to the sleep inertia that makes the level of consciousness of the awakened subject stay low, the level of consciousness of the awakened subject is likely to decrease. In contrast, as shown in FIG. 4, the present inventors found that if the stimulus is provided appropriately, the phase of the cycle of increase and decrease in the sleep depth of the subject can be changed. For example, as shown in FIG. 5, if the time of presenting the stimulus is changed, the time taken for the subject to reach the sleep stage 2 after the end of the presentation of the stimulus can be changed.

Figure 6:
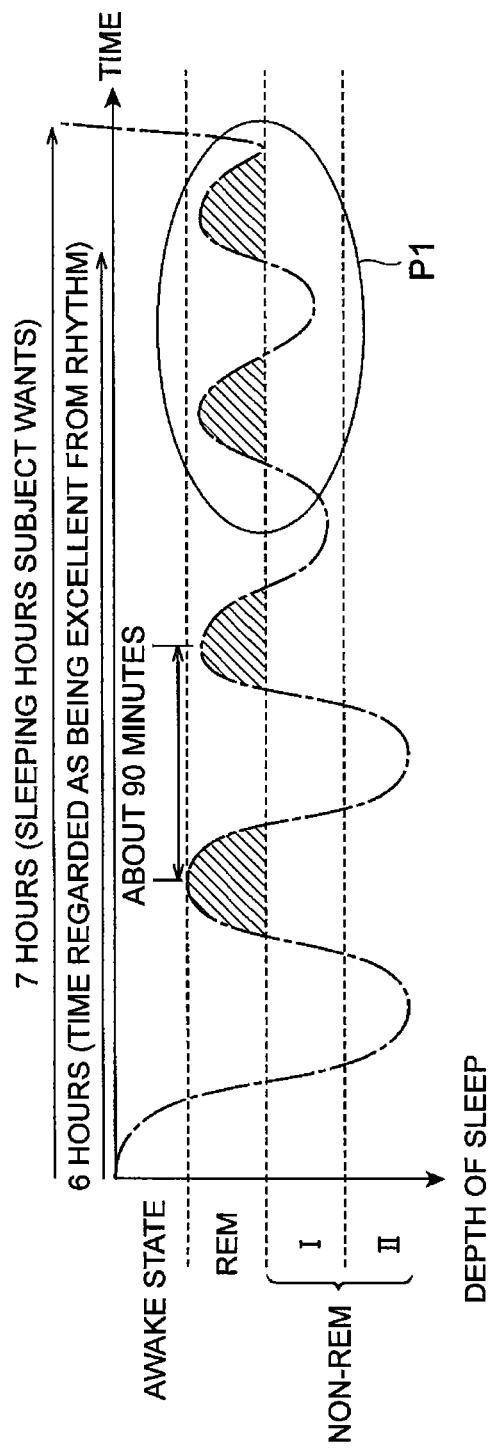
FIG. 6 is a graph showing a cyclical change in the sleep depth.

As shown in FIG. 6, in the ultradian rhythm, one cycle of increase and decrease in the sleep depth ends within a period of about 90 minutes. Accordingly, when the sleeping hours that the subject wants are a multiple of 90 minutes, such as 6 hours, the sleep depth of the subject is minimized at the wake-up time. Consequentially, the sleep inertia is reduced, and the subject can wake up feeling refreshed. However, for instance, when the sleeping hours that the subject wants are 7 hours, which are not a multiple of 90 minutes, the subject wakes up in the transition state in which the sleep depth of the subject further increases. In this case, due to the sleep inertia, the level of consciousness of the awakened subject is likely to decrease.

Figure 7:
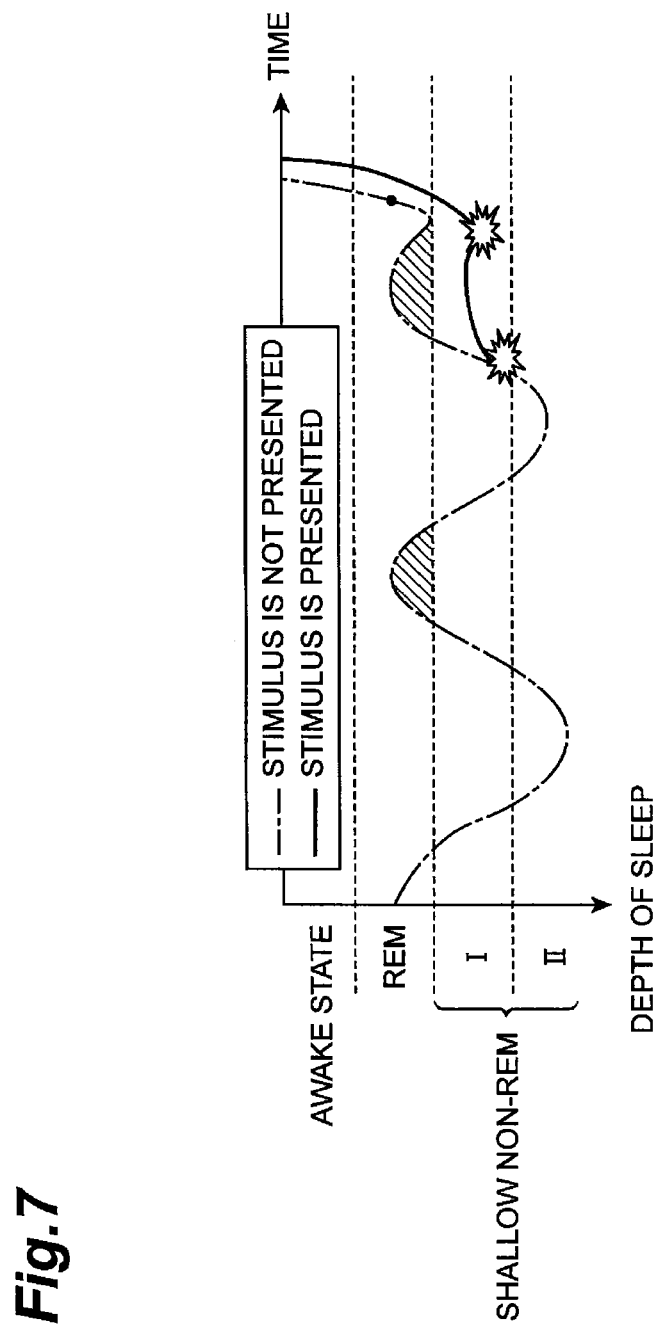
FIG. 7 is a graph showing a change in the sleep depth in a case in which a stimulus is presented in a section P1 of FIG. 6 and in a case in which a stimulus is not presented in the same section.

For this reason, in the present embodiment, as shown in FIG. 3 and FIG. 7 which is an enlarged view of a section P of FIG. 6, before the sleep depth increases, the stimulus presentation device 47, which does not wake the subject up until the wake-up time that the subject wants, presents a stimulus in the section in which the sleep depth decreases, and in this way, the phase of the cycle of increase and decrease in the sleep depth of the subject is shifted (S23). Consequentially, the sleep depth of the subject is minimized at the wake-up time. As a result, the sleep inertia is reduced, and the subject can wake up feeling more refreshed. Herein, the sleep depth of the subject at any point in time can be predicted by using the usual ultradian rhythm of the subject.

Figure 8:
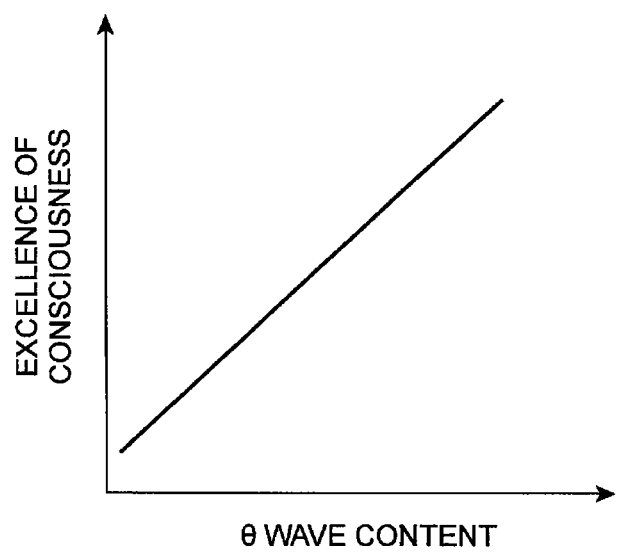
FIG. 8 is a graph showing excellence of consciousness relative to a θ wave content before an awake state.

Herein, as shown in FIG. 8, regarding a nap, for example, during a nap for 20 minutes, 1 minute, which corresponds to 5% of the sleeping hours, before the wake-up time, a relationship is established in which a content of θ waves and the excellence of consciousness are directly proportional to each other. During a sleep for about 6 hours in the night, if the θ waves increase in the spectrum approximately 10 minutes to 20 minutes, which correspond to about 5% of the sleeping hours, before the wake-up time, the sleep inertia of the subject is reduced. The θ waves are background brain waves appearing at the sleep depth corresponding to the sleep stage 1.

Therefore, in the present embodiment, as shown in FIG. 3, when the REM sleep detection portion 43 predicts that the subject may not be in the state of REM sleep at the wake-up time (S24), 10 minutes to 20 minutes before the expected wake-up time of the subject, or, at a time, which is 5% of the total sleeping hours, before the expected wake-up time of the subject, a stimulus is presented to the subject such that the subject progresses into the sleep depth of the sleep stage 1 and the θ waves appear (S25).

At a point in time 10 minutes to 20 minutes before the wake-up time that the subject wants, or, at a point in time, which corresponds to 5% of the total sleeping hours, before the wake-up time that the subject wants, if the subject is in the sleep stage 2, or if the sleep depth of the subject is greater than that of the sleep stage 2, the stimulus presentation device 47 presents a stimulus and thus induces the subject to have shallower sleep, such that the consciousness of the awakened subject becomes excellent. In this case, from the brain waves of the subject, the appearance of the θ waves is confirmed, and it is confirmed that the eye movements of the subject are not in the form of sawtooth waves that are observed in the REM sleep. Moreover, from the respiration of the subject, it is confirmed that the sleep depth of the subject corresponds to the sleep stage 1. The stimulus is presented in each case in which the sleep depth keeps increasing until the wake-up time.

For confirming the appearance of the θ waves from the brain waves, it is possible to use a power spectrum of the θ waves, a ratio between power spectra (sum of spectra of 4 Hz to 8 Hz/sum of spectra of 0.5 Hz to 24 Hz), wavelet transform, and the like. For confirming the appearance of the θ waves by using eye potential, the θ waves can be detected if waves of high amplitude of 1 Hz to 10 Hz appear.

When the subject spontaneously wakes up, the stimulus presentation device 47 does not additionally presents a stimulus and allows the subject to wake up naturally. When the subject does not wake up at the wake-up time, the stimulus presentation device 47 presents a stimulus for waking the subject up, such as a stimulus lasting for 5 seconds to 10 seconds. After the wake-up time, a stimulus such as vibration may be presented at a constant time interval. Furthermore, other types of stimulus such as sound may be presented in combination.

Figure 9:
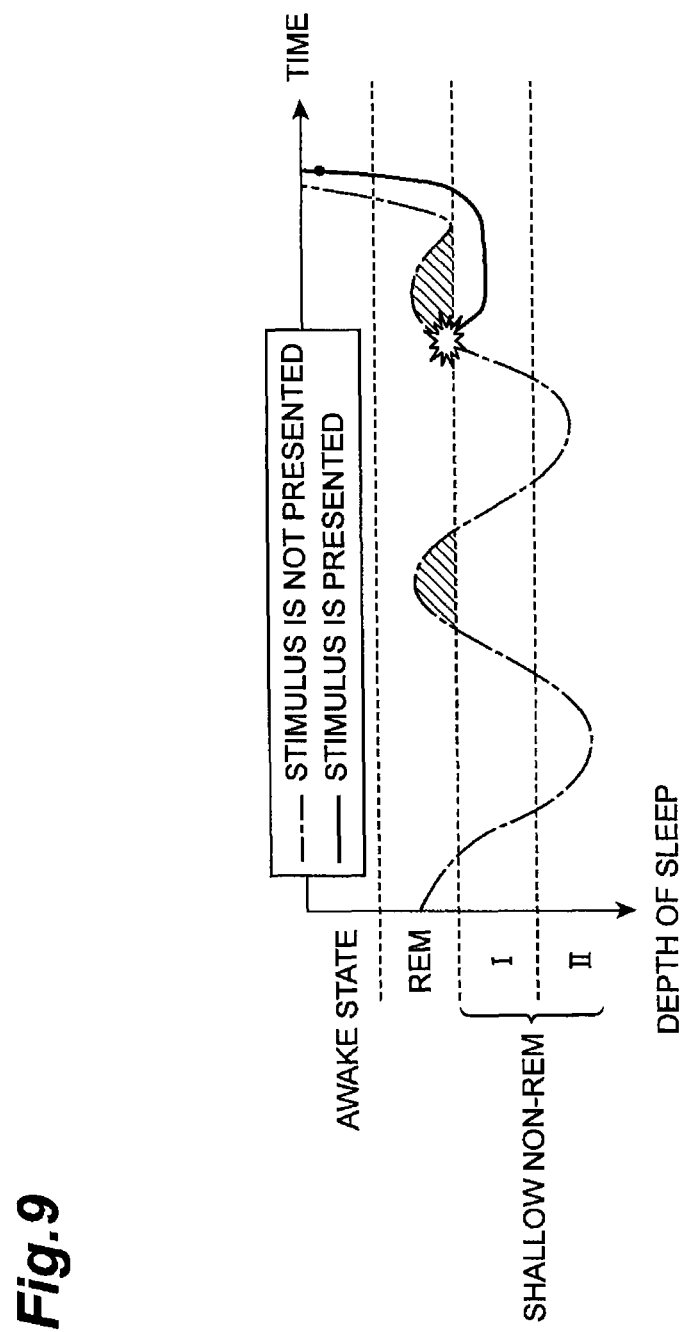
FIG. 9 is a graph showing whether or not the subject has REM sleep in relation to the change in the sleep depth in a case in which a stimulus is presented and in a case in which a stimulus is not presented.

Meanwhile, when the REM sleep detection portion 43 predicts that the subject may be in the state of REM sleep at the wake-up time (S24), the subject is awakened in the following manner in the present embodiment. During the REM sleep, muscles of the subject are relaxed, and the level of consciousness of the subject awakened from the REM sleep tends to be low. However, if all of the REM sleeps of the subject are suppressed throughout the entire sleeping hours, the awakened subject is likely to suffer from excessive daytime sleepiness. Therefore, in the present embodiment, as shown in FIGS. 3 and 9, during the period of the final REM sleep closest to the wake-up time, the subject is inhibited from progressing into the REM sleep from the non-REM sleep (S26).

For example, when the REM sleep detection portion 43 determines that the subject is in the state of REM sleep approximately 30 minutes before the wake-up time, in order to make the awakened subject have excellent consciousness, the stimulus presentation device 47 presents a vibration stimulus or the like, and the REM sleep is selectively suppressed. In a case in which the eye potential in the form of sawtooth waves that are observed in the REM sleep is detected before the wake-up time, a stimulus appropriate for the case is presented, and the REM sleep is suppressed.

By using the eye potential sensor 36 mounted on the cephalic region or using the eyeball camera 35, the REM sleep detection portion 43 images the movement of shadow of the pupil of the subject. In this way, the REM sleep detection portion 43 detects the eye movements of the subject and detects the state of REM sleep of the subject. Whether or not the subject is in the state of REM sleep at any point in time can be predicted by using the usual ultradian rhythm of the subject.

Figure 10:
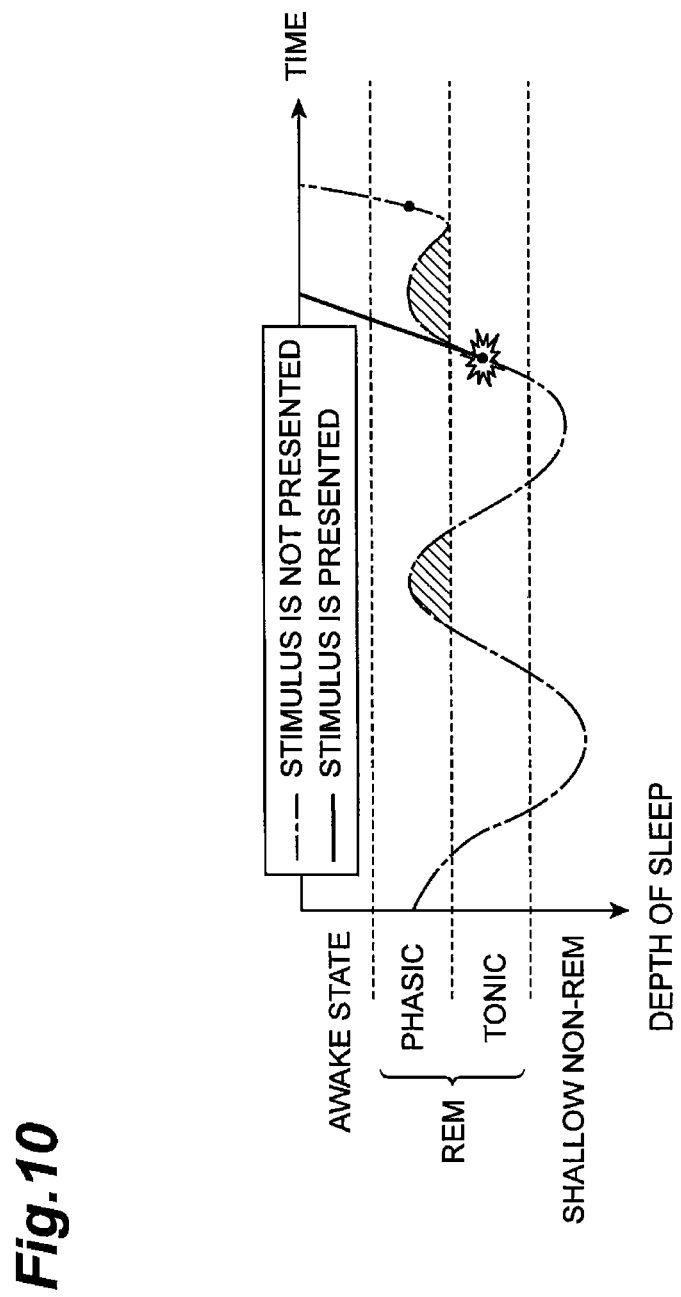
FIG. 10 is a graph showing whether or not the subject has a phasic REM sleep in relation to the change in the sleep depth in a case in which a stimulus is presented and in a case in which a stimulus is not presented.

Alternatively, in the present embodiment, when the REM sleep detection portion 43 predicts that the subject may be in the state of REM sleep at the wake-up time (S24), as shown in FIGS. 3 and 10, a stimulus is presented so as to inhibit the subject from progressing into the phasic REM sleep from the tonic REM sleep (S26).

Figure 11:
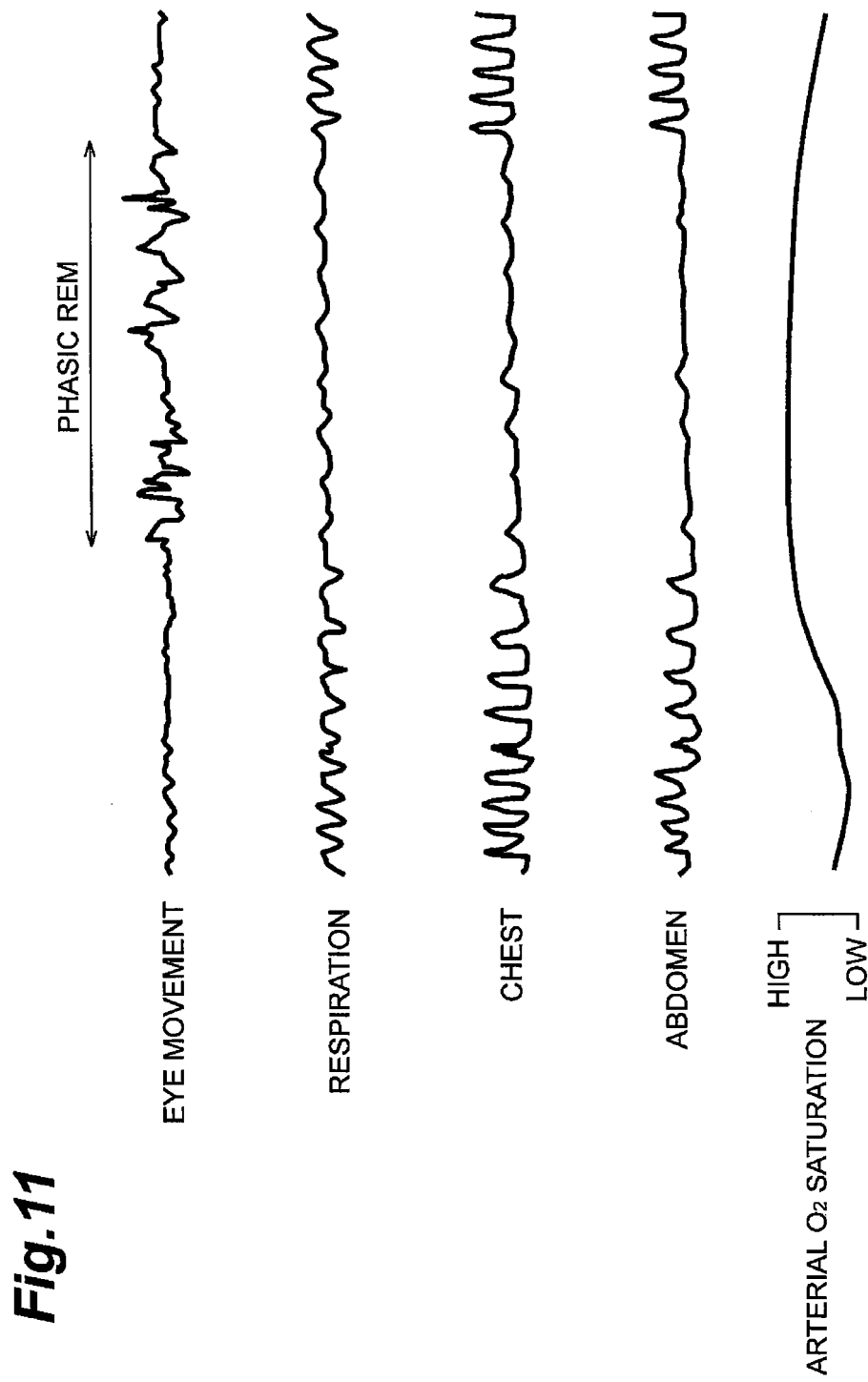
FIG. 11 is a graph showing the eye movements, respiration, chest, abdomen, and arterial oxygen saturation of the subject at the time of the phasic REM sleep.

If the REM sleep is suppressed for an excessively long period of time, the awakened subject is likely to suffer from excessive daytime sleepiness. As shown in FIGS. 10 and 11, the REM sleep includes a phasic period, during which the subject mainly performs eye movements and is in a relaxed state and external stimuli are blocked, and a tonic period during which the subject responds to external stimuli and which is close to the sleep stage 1. Therefore, in the present embodiment, the characteristic amount calculation portion 44 make a differentiation between the phasic REM sleep and the tonic REM sleep. It is possible to prevent the effect of the stimulus presentation from decreasing due to the blocking of stimuli by inhibiting the subject from progressing into the phasic REM sleep from the tonic REM sleep by presenting a stimulus at the tonic phase. And it is possible to reduce the relaxed state of the awakened subject by encouraging the subject to spontaneously wake up by means of presenting a stimulus at the time of shallow sleep.

By using the eye potential sensor 36 mounted on the cephalic region or using the eyeball camera 35, the characteristic amount calculation portion 44 can image the movement of shadow of the pupil of the subject. In this way, the characteristic amount calculation portion 44 can detect the eye movements of the subject and detect the state of tonic REM sleep of the subject. Moreover, by using the variation in the fluctuation of heart rate obtained by the heart rate sensor 37, the characteristic amount calculation portion 44 can detect the state of tonic REM sleep of the subject. Either in a state in which the eye movements are observed or in a state in which the fluctuation of the heart rate increases, the characteristic amount calculation portion 44 determines that the subject is in the state of phasic REM sleep.

When it is determined that the subject is in the state of phasic REM sleep, for example, approximately 10 minutes before the wake-up time, a vibration stimulus is presented to encourage the subject to wake up. Moreover, when the subject starts to have the phasic REM sleep, a stimulus is presented in the same manner. When the eye movements and the fluctuation of heart rate are not observed, and the state of tonic REM sleep lasts, a stimulus is not presented until the wake-up time, and when it is time to wake up, a stimulus for wake the subject up is presented.

Figure 12:
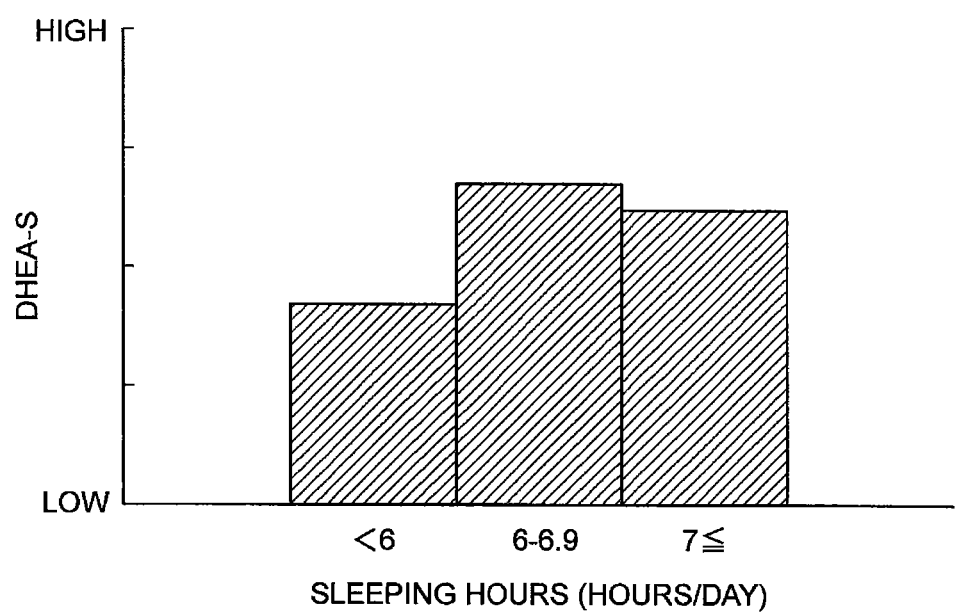
FIG. 12 is a graph showing the level of an adrenocortical hormone relative to sleeping hours.
Figure 13:
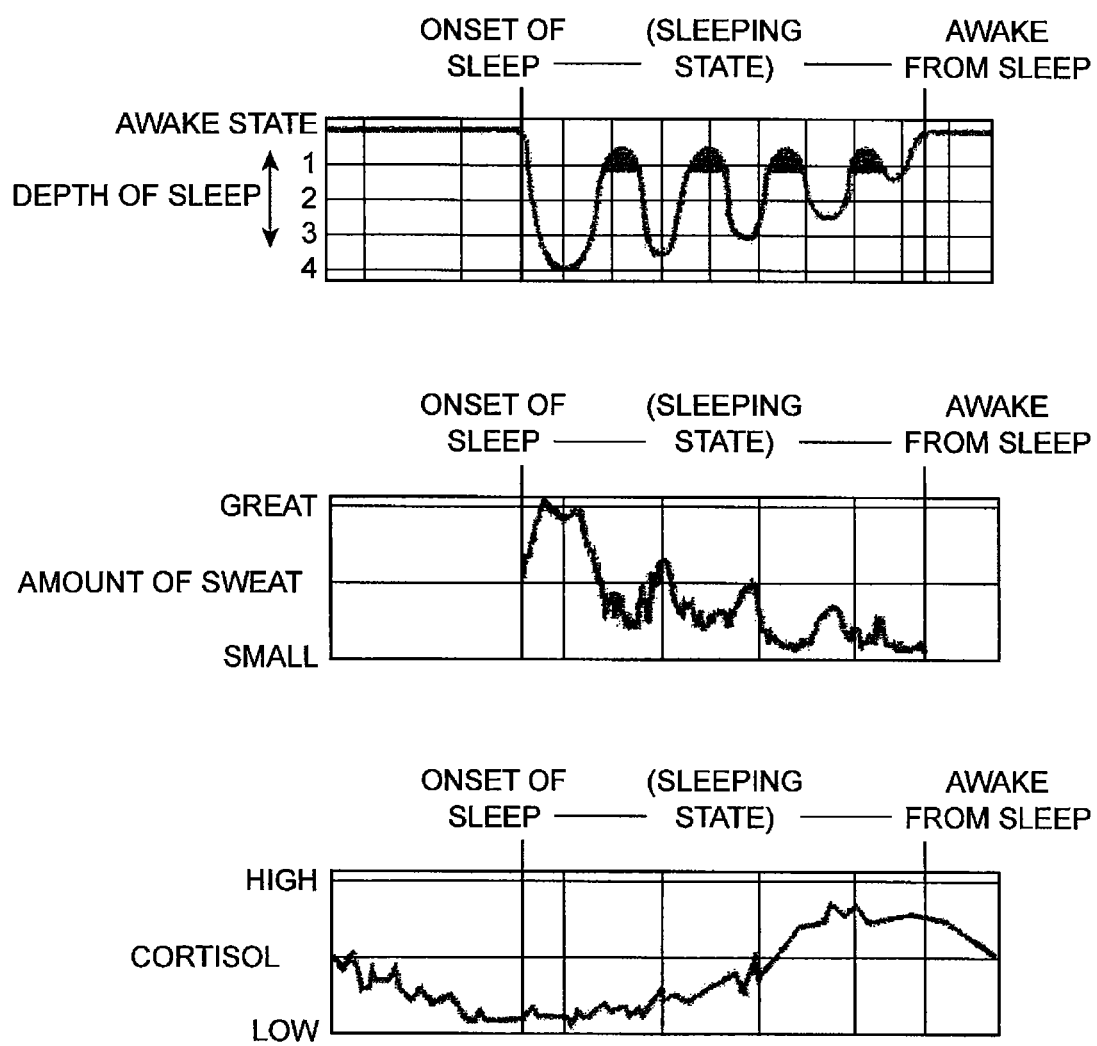
FIG. 13 is a graph showing a change in a sleep depth, an amount of sweat, and a level of cortisol at the time of sleep.
Figure 14:
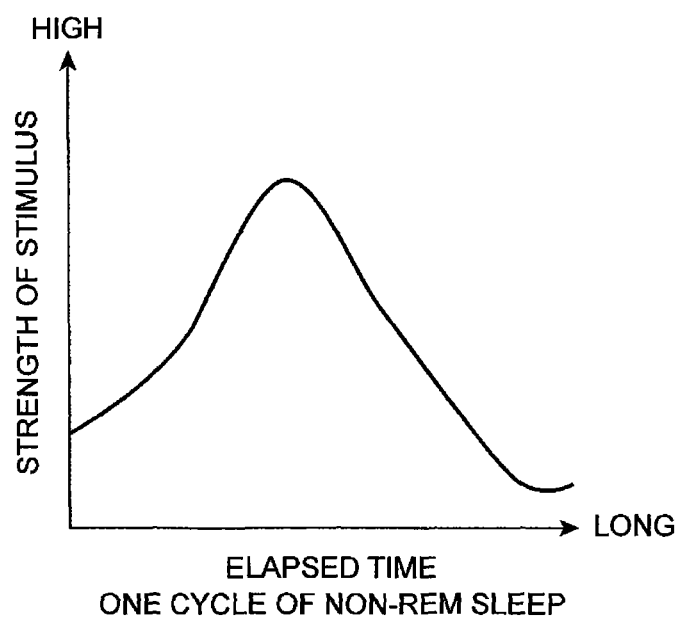
FIG. 14 is a graph showing the strength of a stimulus required for waking the subject up relative to an elapsed time in one cycle of non-REM sleep.
Figure 15:
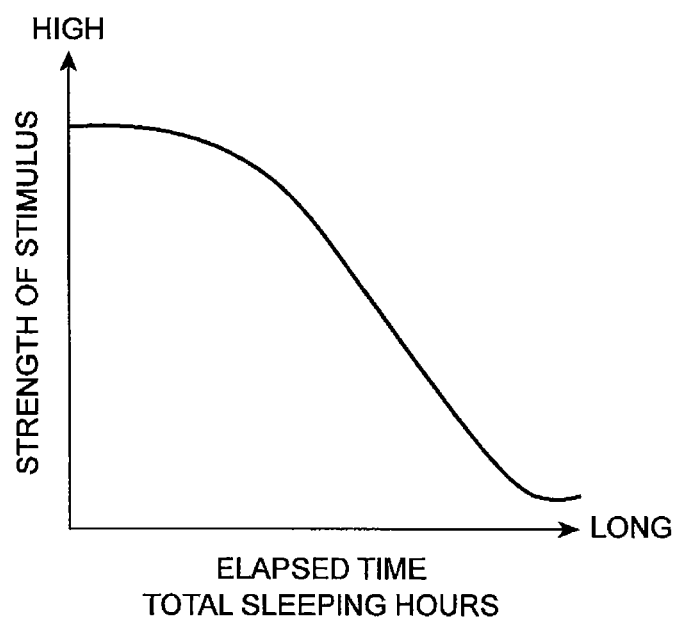
FIG. 15 is a graph showing the strength of a stimulus required for waking the subject up relative to an elapsed time in total sleeping hours.

Hereinafter, the way the stimulus presentation amount determination portion 46 determines the strength of a stimulus in the present embodiment will be described. As shown in FIGS. 12 and 13, the longer the sleeping hours from the onset of sleep, the more the amount of adrenocortical hormones (DHEA-S, cortisol) secreted. The cortisol is a hormone of which the level is heightened at a stage in which the subject is ready to be awakened from the sleep. Due to the cortisol, as shown in FIGS. 14 and 15, the longer the time of sleep elapsed from the onset of the sleep, the weaker the strength of a stimulus necessary for wake the subject up. Therefore, in the present embodiment, the stimulus presentation amount determination portion 46 uses the maps shown in FIGS. 14 and 15, such that as the time of sleep elapsed from the onset of the sleep is lengthened, a weaker stimulus is presented. In this way, it is possible to prevent the subject from being waking up before the wake-up time.

By using the time elapsed from the onset of sleep of the subject that is calculated by the sleep variable calculation portion 42, the stimulus presentation amount determination portion 46 determines the strength of a stimulus at a point in time when the stimulus is to be presented. When a stimulus is presented during the period of non-REM sleep that lasts for 4 hours from the onset of the sleep, the stimulus presentation amount determination portion 46 may determine the strength of a stimulus by using a map of a time zone separated from other time zones. In the case of the vibration stimulus, the strength of the stimulus may be calculated by a function of a frequency, a presentation time, amplitude, and the like. Alternatively, a stimulus may be determined by using a map showing a correlation between the aforementioned numerical values and the time elapsed from the onset of sleep.

Figure 16:
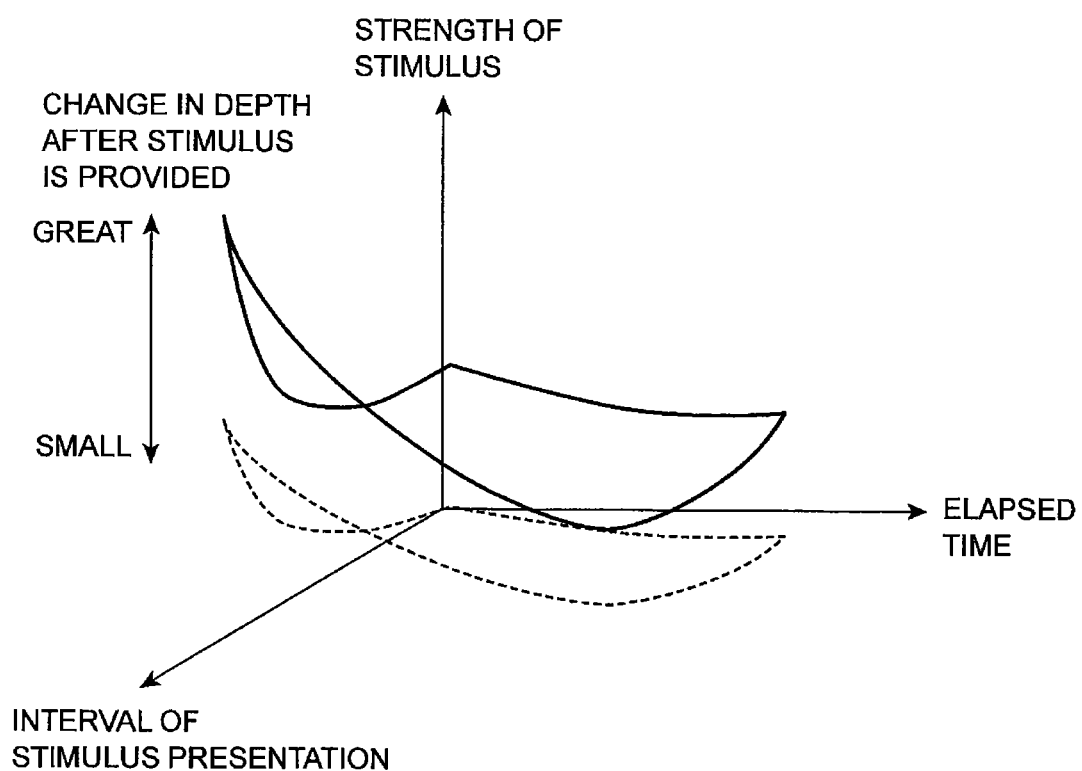
FIG. 16 is a graph showing a relationship among the elapsed time, the strength of a stimulus, and an interval of stimulus presentation.

For example, the stimulus presentation amount determination portion 46 may determine the strength of a stimulus or the presentation method by using a map shown in FIG. 16 showing a correlation among the time elapsed from the onset of sleep, the strength of a stimulus, and the interval of stimulus presentation. As shown in FIG. 16 by a broken line and a solid line, the stimulus presentation amount determination portion 46 may switch the map according to the extent of change in the sleep depth after the first stimulus is presented.

According to the present embodiment, the sleep variable calculation portion 42 predicts the change in the sleep depth of the sleeping subject. Moreover, when the sleep variable calculation portion 42 predicts that the subject may be in a transition state in which the sleep depth of the subject further increases at the wake-up time of the subject, the stimulus presentation device 47 provides a stimulus to the subject at a point in time preceding the wake-up time. Consequentially, the phase of the cycle of the change in the sleep depth of the subject is shifted, and as a result, at the time when the subject is to wake up, the subject is highly likely to be in the transition state in which the sleep depth further decreases instead of the transition state in which the sleep depth further increases. Therefore, the subject is highly likely to be able to wake up feeling more refreshed.

Furthermore, according to the present embodiment, the stimulus presentation device 47 provides a stimulus to the subject, at a point in time predicted as the transition state, in which the sleep depth of the subject further decreases, by the sleep variable calculation portion 42. Consequentially, the phase of the cycle of the change in the sleep depth of the subject is shifted. As a result, the subject is highly likely to be in the transition state, in which the sleep depth of the subject further decreases, even at the time when the subject is to be awakened, and the subject is highly likely to able to wake up feeling more refreshed.

In addition, according to the present embodiment, the stimulus presentation device 47 provides a stimulus that does not wake the subject up until the wake-up time at the time when the stimulus is to be provided. Consequentially, the subject is prevented from waking up before the time when the subject is to be awakened. Moreover, the subject is highly likely to be in the transition state, in which the sleep depth of the subject further decreases, at the wake-up time, and the subject is highly likely to be able to wake up feeling more refreshed.

Moreover, according to the present embodiment, the sleep variable calculation portion 42 predicts the cycle of the change in the sleep depth of the sleeping subject. Furthermore, in the cycle of the change in the sleep depth predicted by the sleep variable calculation portion 42, the stimulus presentation device 47 provides a stimulus to the subject within a period predicted as the transition state in which the sleep depth of the subject further decreases. As a result, the cycle of the sleep depth of the subject is more easily controlled, and the subject is highly likely to be able to wake up feeling more refreshed.

Furthermore, according to the present embodiment, the sleep variable calculation portion 42 predicts the cycle of the change in the sleep depth of the sleeping subject. When the sleep variable calculation portion 42 predicts that the subject may be in the transition state, in which the sleep depth of the subject further increases, at the wake-up time, the stimulus device 47 provides a stimulus to the subject, such that among the periods as the transition states, in which the sleep depth of the subject further increases in the cycle of the change in the sleep depth predicted by the sleep variable calculation portion 42, the period closest to the wake-up time is further shortened. As a result, the period, during which the sleep depth immediately before the time to wake the subject up increases, is shortened, and the sleep inertia that makes the level of consciousness of the awakened subject stay low is reduced. Consequentially, the subject is highly likely to be able to wake up feeling more refreshed.

In addition, in the present embodiment, the stimulus presentation device 47 provides a stimulus to the subject, and in this way, from the stimulus presentation time to the wake-up time, the sleep depth of the subject is maintained at the sleep depth corresponding to the sleep stage 1. In the sleep stage 1, θ waves appear as background brain waves. If the θ waves are caused to appear before the subject wakes up, the sleep inertia that makes the level of consciousness of the awakened subject stay low is reduced, and the subject is highly likely to be able to wake up feeling more refreshed.

Furthermore, in the present embodiment, the REM sleep detection portion 43 predicts the REM sleep period during which the sleeping subject has REM sleep. Based on the REM sleep period predicted by the REM sleep detection portion 43, the stimulus presentation device 47 provides a stimulus to the subject so as to inhibit the subject from progressing into the REM sleep from the non-REM sleep. During the REM sleep, the muscles of the subject are relaxed, and the level of consciousness of the subject awakened from the REM sleep tends to be low. Accordingly, if the subject is inhibited from progressing into the REM sleep from the non-REM sleep, the level of consciousness of the awakened subject can be increased.

Moreover, in the present embodiment, during the REM sleep period closest to the wake-up time among the REM sleep periods predicted by the REM sleep detection portion 43, the stimulus presentation device 47 provides a stimulus to the subject so as to inhibit the subject from progressing into the REM sleep from the non-REM sleep. If the REM sleep of the sleeping subject is excessively suppressed, the level of consciousness of the subject who is awakening is likely to rapidly decrease. Therefore, if the subject is inhibited from progressing into the REM sleep during the REM sleep period closest to the time to wake the subject up among the REM sleep periods of the sleeping subject, it is possible to increase the level of consciousness of the awakened subject, and to prevent the rapid decrease in the level of consciousness of the subject who is awakening.

In addition, according to the present embodiment, the characteristic amount calculation portion 44 predicts the phasic REM sleep period during which the sleeping subject has the phasic REM sleep. Based on the phasic REM sleep period predicted by the characteristic amount calculation portion 44, the stimulus presentation device 47 provides a stimulus to the subject at the second time so as to inhibit the subject from progressing into the phasic REM sleep from the tonic REM sleep. The REM sleep includes a phasic period, during which the subject performs eye movements and external stimuli are blocked, and a tonic phase during which the subject responds to external stimuli and which is close to the sleep stage 1. As described above, if the REM sleep of the sleeping subject is excessively suppressed, the level of consciousness of the subject who is awakening is likely to rapidly decrease. Therefore, in order to reduce the rapid decrease in the level of consciousness of the subject, who is awakening, caused by the excessive suppression of the REM sleep, and to create a state closer to a natural sleep, the subject is inhibited from progressing into the phasic REM sleep from the tonic REM sleep. As a result, it is possible to increase the level of consciousness of the awakened subject, and to prevent the rapid decrease in the level of consciousness of the subject who is awakening.

Furthermore, according to the present embodiment, during the phasic REM sleep period closest to the wake-up time among the phasic REM sleep periods predicted by the characteristic amount calculation portion 44, the stimulus presentation device 47 provides a stimulus to the subject so as to inhibit the subject from progressing into the phasic REM sleep from the tonic REM sleep. As a result, it is possible to create a state closer to a natural sleep, to increase the level of consciousness of the awakened subject, and to prevent the rapid decrease in the level of consciousness of the subject who is awakening.

Moreover, according to the present embodiment, the characteristic amount calculation portion 44 predicts the tonic REM sleep period during which the sleeping subject has the tonic REM sleep, and the stimulus presentation device 47 provides a stimulus to the subject within the tonic REM sleep period predicted by the characteristic amount calculation portion 44. Consequentially, it is possible to inhibit the subject from progressing into the phasic REM sleep while allowing the subject to have the tonic REM sleep. Besides, it is possible to increase the level of consciousness of the awakened subject, and to prevent the rapid decrease in the level of consciousness of the subject who is awakening.

In addition, according to the present embodiment, as the time elapsed from the onset of the sleep of the subject increases, the stimulus presentation device 47 provides a weaker stimulus to the subject. The longer the sleeping hours, the higher the level of the adrenocortical hormone (cortisol). The cortisol is a hormone of which the level is heightened at a stage in which the subject is ready to be awakened from the sleep. The higher the cortisol level, the easier the subject wakes up. Therefore, if the strength of the stimulus is weakened as the sleeping hours increase and as the cortisol level increases, by providing an appropriate stimulus to the subject, it is possible to prevent the subject from waking up before the wake-up time and to control the sleep.

Furthermore, according to the present embodiment, the stimulus presentation device 47 provides a stimulus to the subject, based on the correlation between the time elapsed from the onset of the sleep of the subject at the time when the stimulus is to be presented and the strength of the stimulus. Consequentially, by providing an appropriate stimulus to the subject, it is possible to prevent the subject from waking up before the wake-up time and to control the sleep.

The present invention is not limited to the aforementioned embodiments and can be modified in various ways. For example, in the aforementioned embodiments, the time when a stimulus is presented to the subject and the wake-up time are set to be a certain point in time, but they may be in a time zone having a predetermined width. In this case, a time zone in which a stimulus is presented to the subject and a time zone in which the subject wakes up can be set to have different lengths of time. Furthermore, in the time zone in which a stimulus is presented to the subject, the stimulus may be continuously or intermittently presented to the subject.

INDUSTRIAL APPLICABILITY

According to the sleep control device and the sleep control method of an embodiment of the present invention, the subject is highly likely to be able to wake up feeling more refreshed.

REFERENCE SIGNS LIST

10 wake-up assisting system
20 wake-up time input device
22, 26 network
24 server
30 bio-information measurement device group
31 brain wave sensor
32 respiration sensor
33 skin potential sensor
34 body temperature detection sensor
35 eyeball camera
36 eye potential sensor
37 heart rate sensor
38 blood pressure sensor
40 mobile communication terminal
41 sleep state calculation portion
42 sleep variable calculation portion
43 REM sleep detection portion
44 characteristic amount calculation portion
45 wake-up method determination portion
46 stimulus presentation amount determination portion
47 stimulus presentation device

The invention claimed is:
1. A sleep control device, comprising:
a processor programmed to:
predict a change in a sleep depth of a sleeping subject;

provide a stimulus to the subject at a second time preceding a first time, when the predicting the change has predicted that the subject may be in a transition state in which the sleep depth of the subject further increases at the first time that is set to wake the subject up;

predict a phasic REM sleep period during which the sleeping subject has a phasic REM sleep, and provide the stimulus to the subject at the second time so as to inhibit the subject from progressing into the phasic REM sleep from a tonic REM sleep based on the predicted phasic REM sleep period.

2. The sleep control device according to claim 1, wherein the processor is further programmed to:

predict a plurality of phasic REM sleep periods during which the sleeping subject has the phasic REM sleep, and provide the stimulus to the subject at the second time so as to inhibit the subject from progressing into the phasic REM sleep from the tonic REM sleep during a phasic REM sleep period, among the predicted phasic REM sleep periods, that is closest to the first time.

3. The sleep control device according to claim 1, wherein the processor is further programmed to predict a tonic REM sleep period during which the sleeping subject has the tonic REM sleep, and the second time is included in the predicted tonic REM sleep period.

4. The sleep control device according to claim 1, wherein the second time is predicted as a transition state in which the sleep depth of the subject further decreases.

5. The sleep control device according to claim 1, wherein the processor is further programmed to provide the stimulus, which does not wake the subject up until the first time, at the second time.

6. The sleep control device according to claim 1, wherein the processor is further programmed to predict a cycle of a change in the sleep depth of the sleeping subject, and the second time is included in a sleep depth decreasing period predicted as a transition state in which the sleep depth of the subject further decreases in the predicted cycle of the change in the sleep depth.

7. The sleep control device according to claim 1, wherein the processor is further programmed to:

predict a cycle of a change in the sleep depth of the sleeping subject, and provide the stimulus to the subject at the second time, such that a sleep depth increasing period closest to the first time, among sleep depth increasing periods as the transition state in which the sleep depth of the subject further increases in the predicted cycle of the change in the sleep depth, is further shortened when it is predicted that the subject may be in the transition state in which the sleep depth of the subject further increases at the first time.

8. The sleep control device according to claim 1, wherein the processor is programmed to provide a weaker stimulus to the subject as a time elapsed from an onset of sleep of the subject increases.

9. The sleep control device according to claim 1, wherein the processor is further programmed to provide the stimulus to the subject at the second time based on a correlation between a time elapsed from an onset of sleep of the subject at the second time and a strength of the stimulus.

* * * * *